(12) United States Patent
Harvey et al.

(10) Patent No.: US 10,604,711 B1
(45) Date of Patent: Mar. 31, 2020

(54) ALKYL CYCLOBUTANE FUELS

(71) Applicant: The United States of America, as represented by the Secretary of the Navy, Arlington, VA (US)

(72) Inventors: Benjamin G. Harvey, Ridgecrest, CA (US); David Morris, Ridgecrest, CA (US)

(73) Assignee: The United States of America, as Represented by the Secretary of the Navy, Washington, DC (US)

( * ) Notice: Subject to any disclaimer, the term of this patent is extended or adjusted under 35 U.S.C. 154(b) by 9 days.

(21) Appl. No.: 16/059,963

(22) Filed: Aug. 9, 2018

(51) Int. Cl.
  *C10L 1/16* (2006.01)
  *C07C 2/24* (2006.01)
  *C07C 13/06* (2006.01)

(52) U.S. Cl.
  CPC ............... *C10L 1/1608* (2013.01); *C07C 2/24* (2013.01); *C07C 13/06* (2013.01); *C07C 2531/22* (2013.01)

(58) Field of Classification Search
  CPC combination set(s) only.
  See application file for complete search history.

(56) References Cited

U.S. PATENT DOCUMENTS 2,753,380 A * 7/1956 Pines .................. C07C 31/1336
            585/317
2018/0251702 A1* 9/2018 Bredsguard ........ C10M 169/045

* cited by examiner

*Primary Examiner* — Ellen M McAvoy
*Assistant Examiner* — Chantel L Graham
(74) *Attorney, Agent, or Firm* — Naval Air Warfare Center Weapons Division; Matthew D. Pangallo (57) ABSTRACT

A method for making an alkyl cyclobutane fuel, which includes obtaining a solution of at least one alpha olefin. A catalyst is added to the solution, thereby generating a mixture of dimers. The mixture is hydrogenated, thereby converting the dimers to hydrogenated dimers. The mixture is purified to produce an alkyl cyclobutane fuel.

25 Claims, 5 Drawing Sheets

ALKYL CYCLOBUTANE FUELS

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND

Fuel precursors can be chemically produced from petroleum and bio-based sources or obtained from naturally occurring crude oil sources. When producing fuel, the precursors are added to a distillation column with a temperature gradient to separate the various hydrocarbon molecules within the fuel precursor. The hydrocarbon molecules are separated by size and subjected to a specific treatment to produce a fuel for a specific application. For example, jet fuel may contain a mixture of hydrocarbons ranging from 5 to 16 carbon atoms in each molecule. These hydrocarbons are separated from the column after boiling and specifically treated to produce jet fuel. As a result, distilling a fuel precursor may produce a variety of fuels for different applications in a single distillation.

BRIEF DESCRIPTION OF THE DRAWINGS

Features and advantages of examples of the present disclosure will be apparent by reference to the following detailed description and drawings, in which like reference numerals correspond to similar, though potentially not identical, components. For the sake of brevity, reference numerals or features having a previously described function may or may not be described in connection with other drawings in which they appear.

DETAILED DESCRIPTION

In general, fuel precursors that are small hydrocarbon molecules have lower boiling points while larger hydrocarbon molecules have higher boiling points. Typically, petroleum based fuels are produced by distillation of crude oil as the fuel precursor. The portion of the low boiling distillate is used for gasoline, the portion of the mid-range boiling point distillate is used for jet fuel, the portion of higher boiling point distillate is used for diesel fuel, and the portion of highest boiling point distillate is used for lubricants. As a result, only a fraction of the distilled product can be used for a specific purpose (e.g., jet fuel vs. diesel fuel).

In the disclosure herein, it has been advantageously found that by reacting certain compounds with catalysts that are selective for dimer formation, specific hydrocarbons can be produced and used as jet fuel. As a result, the distillate of the hydrocarbons produced from the method herein produce a single product used for jet fuel rather than multiple fuel products used in a variety of applications. The fuel produced herein that includes alkyl cyclobutanes has an increased density, an increased volumetric net heat of combustion, a decreased viscosity, and a lower freezing point compared to fuel produced from conventional acyclic paraffins that have a similar molecular weight.

The present disclosure herein includes methods for making alkyl cyclobutane fuels. In an example, the method includes obtaining a solution of at least one alpha olefin, adding a catalyst to the solution, thereby generating a mixture of dimers, hydrogenating the mixture to convert the dimers to hydrogenated dimers, and purifying the mixture to produce an alkyl cyclobutane fuel. In another example, the method includes obtaining a solution of at least one alpha olefin, adding a catalyst to the solution, thereby generating a mixture of at least one alkyl cyclobutane, and purifying the mixture to produce an alkyl cyclobutane fuel.

Figure 1:
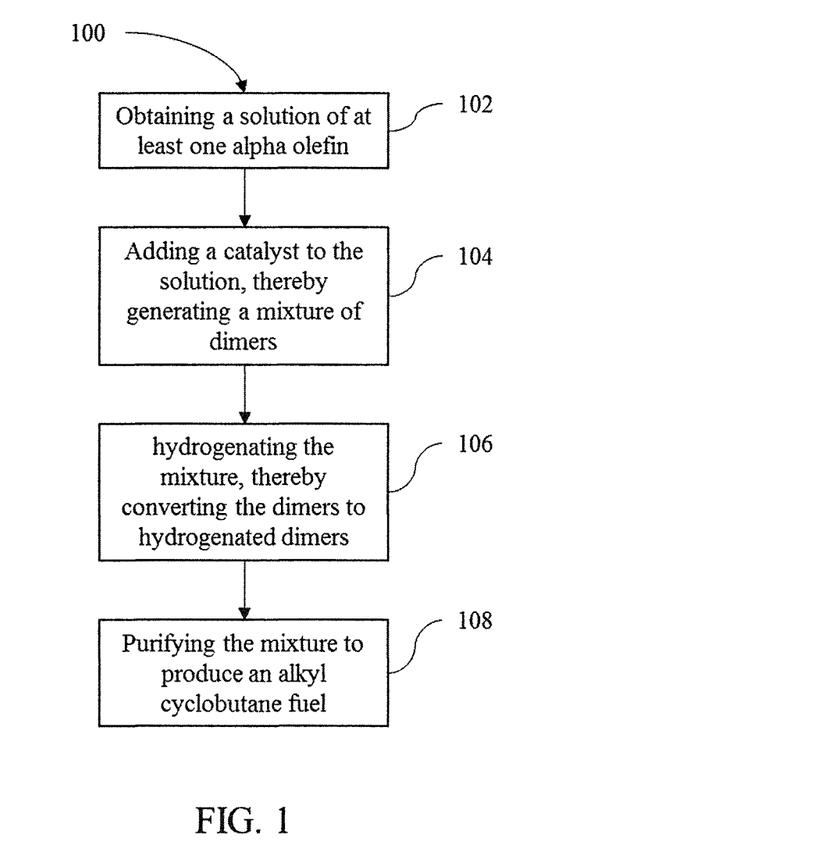
FIG. 1 is a flow diagram illustrating an example of a method of making an alkyl cyclobutane fuel described herein.

Referring now to FIG. 1, the method 100 of making an alkyl cyclobutane fuel includes a first step 102 of obtaining a solution of at least one alpha olefin. Alpha olefins function as reactive compounds to form hydrocarbon chains that may be used in fuel production. In addition, alpha olefins may be produced from petroleum-based sources or bio-based sources, which allow for sustainable production. Any bio-based source may be used that can produce alpha olefins, such as lignocellulosic biomass. In some instances, using alpha olefins to make hydrocarbon chains from bio-based sources allow alpha olefins to be more environmentally friendly compared to compounds that cannot be obtained from bio-based sources. Moreover, short chain alpha olefins have low-boiling points, which can reduce separation costs during fuel production.

The alpha olefins may be a solution of a single alpha olefin or a mixture of two or more alpha olefins. The alpha olefins may include carbon atoms present in an amount ranging from about 3 carbon atoms to about 40 carbon atoms. In other examples, the carbon atoms are present in an amount ranging from about 3 carbon atoms to about 20 carbon atoms. Some examples of alpha olefins include, ethylene, propylene, 1-butene, 1-pentene, 1-hexene, 1-heptene, 1-octene, 1-nonene, 1-decene, and combinations thereof.

In other examples, the alpha olefin may have at least one hydrocarbon chain branch. The hydrocarbon chain branching may include a range of a 3 carbon ring system to a 10 carbon ring system. For example, the alpha olefin may be a vinyl or allyl group having cyclic substituents. Some examples of alpha olefins with at least one hydrocarbon chain branch include, but are not limited to, isoprene, vinylcyclobutane, allylcyclobutane, vinylcyclopropane, allylcyclopropane, vinylcyclopentane, allylcyclopentane, vinylcyclohexane, allylcyclohexane, 3-methylbut-1-ene, α-olefin branched chain isomers of 1-hexene, 1-heptene, 1-octene, 1-nonene, and 1-decene, and combinations thereof.

In particular, the alpha olefins herein may be derived by any known methods from petroleum-based sources or bio-based sources. Some methods include using pyrolysis, fermentation, or conversion of biomass sources to synthesis gas, followed by Fischer-Tropsch catalysis to generate alpha olefins from biomass. Bio-based alpha olefins can also be derived by fermentation of biomass sugars or lignin with microorganisms. In an example, ethylene, propylene, 1-butene, 1-pentene, 1-hexene can generated by dehydration of ethanol, propanol, n-butanol, n-pentanol, and n-hexanol, respectively. In another example, 1-hexene may be derived from ethylene trimerization or hydrogenation of caproic acid. In yet another example, isoprene is derived from dehydration of 2-methyl-3-butene-2-ol. In a further example, isoprene is directly generated by fermentation and continuously removed from the fermentation broth by low temperature distillation.

Referring back to method 100, the following step 104 includes adding a catalyst to the solution of at least one alpha olefin, thereby generating a mixture of dimers. The catalyst selectively forms dimers from the hydrocarbons in the mixture while avoiding the formation of heavier oligomers. Therefore, selectively forming dimers produces a single product, which can be refined into jet fuel, rather than multiple products that are refined into different fuels. This also removes the necessity of converting high-boiling point products to low-boiling point products to obtain a single product that can be refined into jet fuel. Additionally, formation of product mixtures rich in alkyl cyclobutanes reduce the hydrogen demands for fuel production, leading to reduced costs in fuel production and a more sustainable process.

Figure 2:
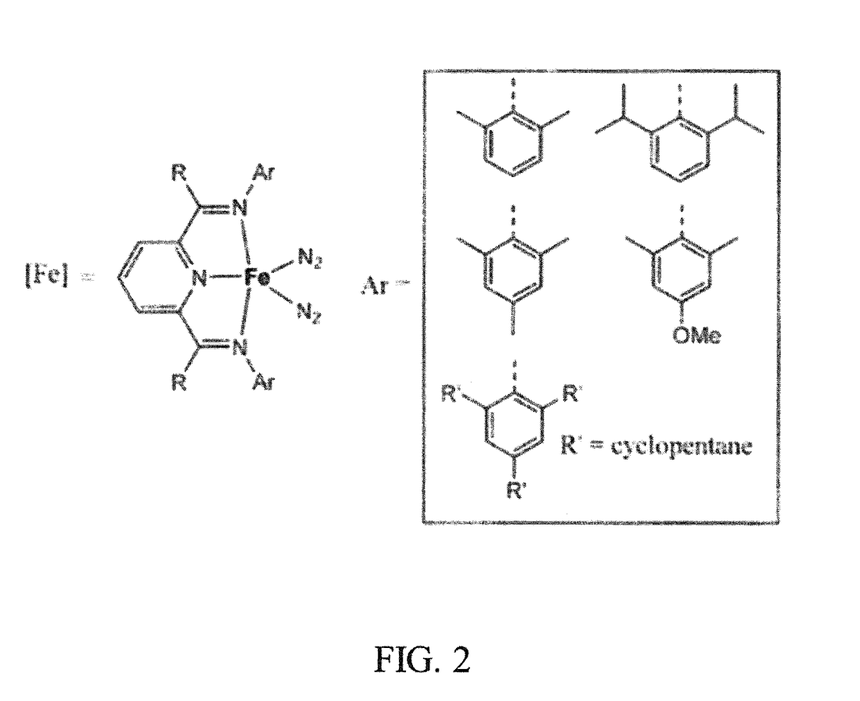
FIG. 2 is an example of a chemical structure of a catalyst coordinated to a pyridine diimine pincer ligand used to generate a mixture of hydrocarbons.

In an example, the catalyst may be an Fe-based or a Co-based catalyst. In other examples, the Fe-based or Co-based catalyst is coordinated to a pyridine (diimine) pincer ligand. In some examples, the ligand is connected to an inorganic support or polymer support. FIG. 2 shows an example of the chemical structure of the Fe-based catalyst coordinated to a pyridine diimine pincer ligand. The R groups in FIG. 2 may be any aliphatic group, aromatic group, fluorinated aliphatic group, fluorinated aromatic group, or combinations thereof. For example, methyl, ethyl, or trifluoromethyl groups can be used. The Ar groups may be any one of the aromatic hydrocarbons shown in FIG. 2. In other examples, the Ar groups may have R' groups in the ortho positions only, para position only, or in both the ortho positions and para position. In some further examples, the Ar groups can be aromatic groups with electron donating groups (e.g., methoxy), or electron withdrawing groups (e.g., a trifluoromethyl group).

In step 104, the catalyst generates a mixture of dimers, where the dimers may be alkyl cyclobutanes or a combination of alkyl cyclobutanes and alkene dimers. It is believed that the alkyl cyclobutanes increase the density and volumetric net heat of combustion in fuel mixtures. As a result, the alkyl cyclobutanes increase the efficiency of the jet fuel by causing less fuel to burn for a given release of heat energy. In one example, the alkene dimers may be removed from the mixture of dimers using any known methods, such as distillation, to include only alkyl cyclobutanes remaining in the mixture of dimers. Some examples of alkyl cyclobutanes include 1,2-alkylcyclobutane, 1,3-alkylcyclobutane, or combinations thereof.

In some examples, the mixture of dimers includes the alkyl cyclobutanes present in an amount ranging from about 50% to about 98% based on a total % of dimers in the mixture of dimers. In another example, the alkyl cyclobutanes are present in an amount ranging from about 50% to about 80% based on a total % of the dimers. In yet another example the alkyl cyclobutanes are present in an amount ranging from about 80% to about 98% based on a total % of the dimers.

In other examples of step 104, alkene dimers may be produced to form a combination of alkyl cyclobutanes and alkene dimers. It is believed the alkene dimers decrease the viscosity and lower the freezing point of the alkyl cyclobutane fuel. As such, when the alkene dimers are present in the fuel, the alkene dimers reduce fuel consumption by increasing the gravimetric net heat of combustion and reduce the likelihood of the fuel freezing. In some examples, the mixture of dimers includes alkene dimers present in an amount ranging from about 1% to about 50% based on a total % of the dimers in the mixture of dimers. The alkene dimers generated vary depending on the alpha olefin used in the reaction. Some examples of general formulas (i, ii) for the alkene dimers are shown below:

where R, R', R" can each individually be any alkyl or cycloalkane group with the amount of carbons ranging from about 4 carbons to about 16 carbons. Some specific examples of alkene dimers that may be generated include 4-methyl-5-methyleneoctane, 5-methyl-6-methyleneoctane, and combinations thereof.

The reaction time between the catalyst and at least one alpha olefin may vary depending on the loading of the catalyst. In addition, different catalysts may yield different product distributions. The reaction may be conducted neat or in the presence of a solvent, such as aromatic solvents (e.g., benzene, toluene), cycloalkanes (e.g., cyclohexane, methylcyclohexane). In examples of the method herein, the catalyst may be reacted with at least one alpha olefin for a time ranging from about 1 hour to about 150 hours at a temperature ranging from about 0° C. to about 80° C.

In some examples, the catalyst may be added to the solution of at least one alpha olefin under pressure to increase the yield of alkyl cyclobutanes in the mixture of dimers. It is believed that there is a direct correlation between increasing the pressure and increasing the percent of alkyl cyclobutanes in the mixture of dimers. The reaction of the catalyst with the alpha olefin or mixture of alpha olefins may occur at a pressure ranging from about 1 atm to about 400 atm.

The temperature and time of the reaction occurring under pressure may be the same as previously mentioned herein.

Referring back to FIG. 1, after the reaction between the catalyst and the alpha olefin or mixture of alpha olefins, the next step 106 includes hydrogenating the mixture, thereby converting the dimers to hydrogenated dimers. In particular, step 106 removes double bonds from the mixture of dimers to convert residual alkenes to alkanes and prepare the mixture of dimers for purification. For example, alkene dimers that may be present in the mixture of dimers form branched alkanes after saturation.

In an example, hydrogenating the mixture may be performed via hydrogenation in the presence of hydrogen gas with a catalyst based on a transition metal. The transition metal may be selected from the group consisting of Ni, Pd, Pt, Ru, Cu, Zn, and combinations thereof. Hydrogenating the mixture may be performed at a pressure ranging from about 1 atm to about 200 atm and a temperature ranging from about 25° C. to about 200° C. The amount of time the mixture undergoes hydrogenation may vary depending on the catalyst loading. In examples of the method herein, the mixture may be hydrogenated for a time ranging from about 30 minutes to about 48 hours.

Referring back to FIG. 1, after hydrogenating the mixture, the next step 108 includes purifying the mixture to produce an alkyl cyclobutane fuel. Any known method of purification may be used to purify the mixture. In an example, distillation may be used to purify the mixture. After purification, the fuel can be stored for later use.

In some examples, the alkyl cyclobutane fuel produced from the method 100 herein may be a tricyclic fuel. The tricyclic fuel may have the following formula:

where R and R' are independent of each other and can be cyclopropyl, cyclobutyl, cyclopentyl, cyclohexyl, —CH$_2$-cyclopropyl, —CH$_2$-cyclobutyl, —CH$_2$-cyclopentyl, —CH$_2$-cyclohexyl, or combinations thereof. The alkyl cyclobutane fuel produced from method 100 may have a density of greater than 0.767 g/mL, a volumetric net heat of combustion of greater than 120.0 kBtu/gal, a gravimetric net heat of combustion of greater than 42.8 MJ/kg, a kinematic viscosity at −20° C. of less than 4.78 mm$^2$ s$^{-1}$, and a freezing point of less than −80° C.

Figure 3:
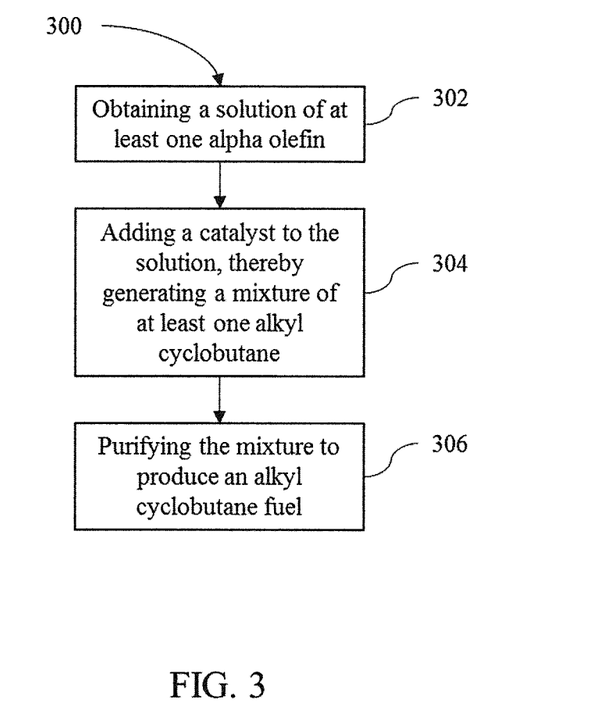
FIG. 3 is another flow diagram illustrating an example of a method of making an alkyl cyclobutane fuel described herein.

Referring now to FIG. 3, the method 300 of making an alkyl cyclobutane fuel includes a first step 302 of obtaining a solution of at least one alpha olefin. The step 302 may be performed as previously described herein in reference to method 100, step 102.

After step 302, the next step 304 includes adding a catalyst to the solution, thereby generating a mixture of at least one alkyl cyclobutane. In one example of step 304, the catalytic reaction generates 98% alkyl cyclobutanes in the mixture. In this example of step 304, the alkene dimers may be removed from the mixture of dimers using any known methods, such as distillation. Removing the alkene dimers forms a mixture of alkyl cyclobutane dimers that are present in an amount of 100% based on a total % of the dimers in the mixture. It is believed that when generating a mixture with 100% alkyl cyclobutanes, a saturated mixture is obtained without any additional steps. Therefore, the method 300 includes no hydrogenation step. In step 304, as an example, the catalyst may be the same catalyst as previously described herein in FIG. 2, step 104.

The reaction time between the catalyst and at least one alpha olefin may vary depending on the loading of the catalyst. In addition, different catalysts may yield different product distributions. The reaction may be conducted neat or in the presence of a solvent, such as aromatic solvents (e.g., benzene, toluene), cycloalkanes (e.g., cyclohexane, methylcyclohexane). In examples of the method herein, the catalyst may be reacted with at least one alpha olefin for a time ranging from about 1 hour to about 150 hours at a temperature ranging from about 0° C. to about 80° C.

In some examples, the catalyst may be added to the solution of at least one alpha olefin under pressure to increase the yield of alkyl cyclobutanes in the mixture of at least one alkyl cyclobutane. It is believed that there is a direct correlation between increasing the pressure and increasing the percent of alkyl cyclobutanes in the mixture of dimers. The reaction of the catalyst with the alpha olefin or mixture of alpha olefins may occur at a pressure ranging from about 1 atm to about 400 atm to generate at least one alkyl cyclobutane. Some examples of alkyl cyclobutanes that are generated include 1,2-alkylcyclobutane, 1,3-alkylcyclobutane, or combinations thereof.

Referring back to FIG. 3, after reacting the alpha olefin or mixture of alpha olefins with the catalyst, the next step 306 includes purifying the mixture to produce an alkyl cyclobutane fuel. Any known method of purification may be used to purify the mixture. In an example, distillation may be used to purify the mixture. After purification, the fuel can be stored for later use. It is to be understood that the tricyclic fuel described here in reference to FIG. 1, step 108 may also be produced from the method 300 shown in FIG. 3.

To further illustrate the present disclosure, examples are given herein. It is to be understood that these examples are provided for illustrative purposes and are not to be construed as limiting the scope of the present disclosure.

EXAMPLES

Scheme of Cyclobutane Fuels

Figure 4:
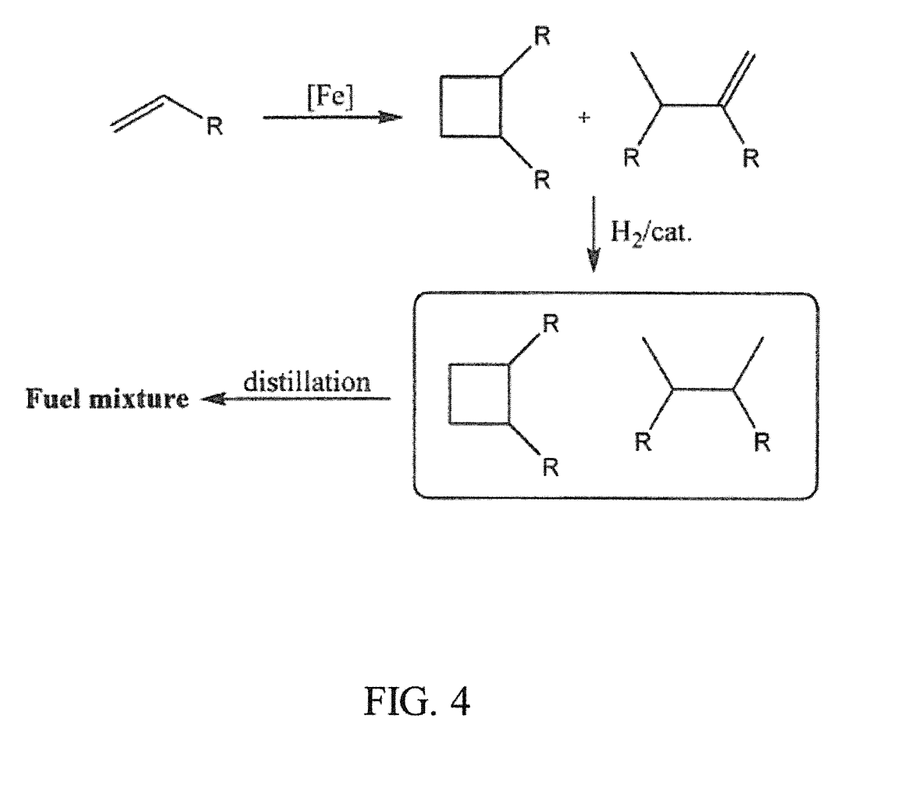
FIG. 4 is a scheme illustrating an example of a method of making an alkyl cyclobutane fuel described herein.
Figure 5:
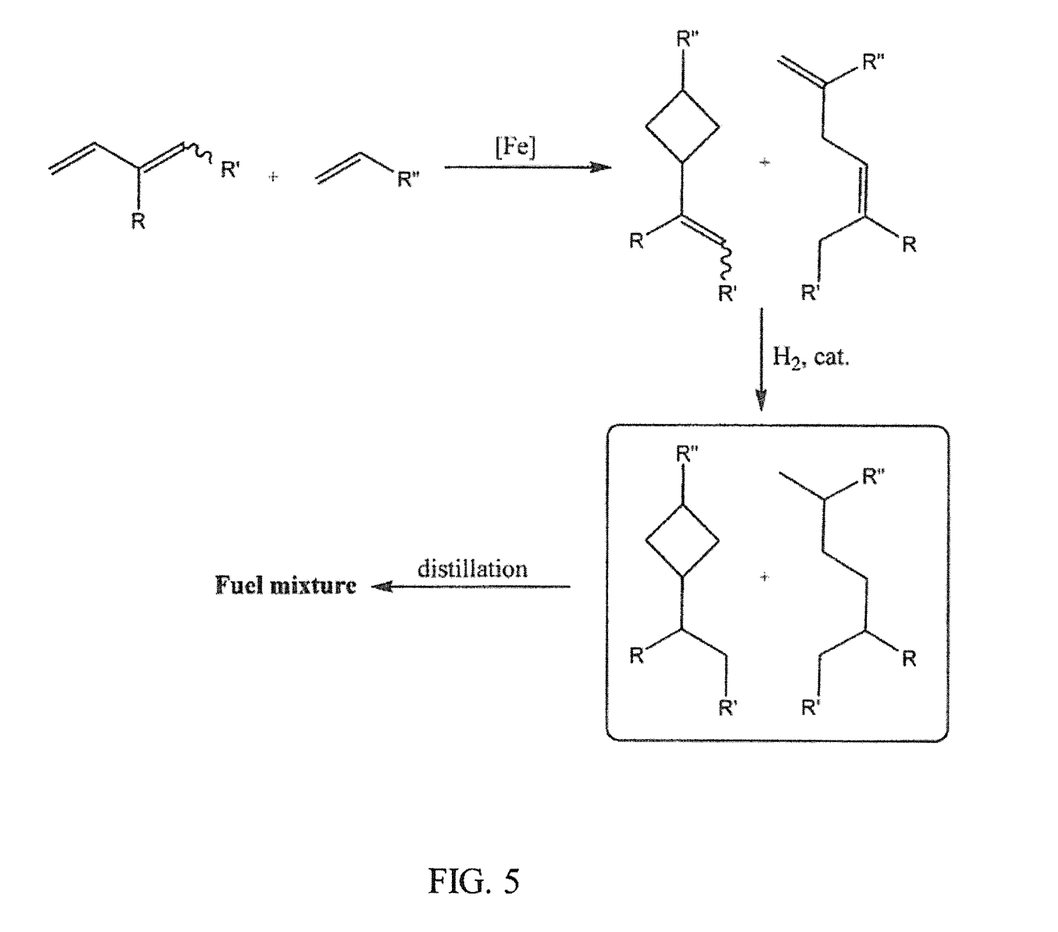
FIG. 5 is another scheme illustrating an example of a method of making an alkyl cyclobutane fuel described herein.

FIG. 4 and FIG. 5 show different schemes of methods for producing an alkyl cyclobutane fuel herein. In FIG. 4, a single alpha olefin solution is reacted with an Fe catalyst. In FIG. 5, the solution contains a mixture of two different alpha olefins that are reacted with an Fe catalyst. Both schemes show an Fe-catalyzed [2+2] cycloaddition that result in the formation of an alkyl cyclobutane and an alkene dimer. FIG. 4 and FIG. 5 both illustrate the removal of double bonds after the mixture of hydrocarbons is hydrogenated, followed by distillation to form a fuel mixture. In one example, in FIG. 4, R can be any alkyl group. In another example, in FIG. 4 and FIG. 5, R, R', and R" can be independent of each other and represent cyclopropyl (CP), cyclobutyl (CB), cyclopentyl (CPE), cyclohexyl, —CH$_2$—CP, —CH$_2$—CB, —CH$_2$—CPE, or —CH$_2$— cyclohexyl. In yet another example, the R, and R" can be acyclic groups or cyclic alkanes.

Preparation of Catalysts

The pyridine diimine pincer ligand (1E,1'E)-1,1'-(pyridine-2,6-diyl)bis(N-(4-methoxy-2,6-dimethylphenyl)ethan-1-imine) ($^{p\text{-}methoxy}$PDI) was synthesized. 2,6-diacetylpyridine (3.000 g, 18.40 mmol) and 4-methoxy-2,6-dimethylaniline (6.260 g, 41.40 mmol) were added into a flask with a catalytic amount of p-toluene sulfonic acid. The flask was equipped with a reflux condenser and a Dean Stark trap and refluxed for 18 hours in 125 mL of toluene. The solvent was removed under reduced pressure and the mixture was recrystallized from ethanol at −30° C. The yellow product was then collected on a frit, washed with cold ethanol, and dried overnight in a vacuum oven at 100° C. The yield was 4.572 g (58%).

After the ligand was synthesized, an Fe-based precatalyst ($^{p\text{-}methoxy}$PDI)(FeCl$_2$) was prepared. FeCl$_2$ (1 g, 7.89 mmol) and $^{p\text{-}methoxy}$PDI (3.559 g, 8.28 mmol) were loaded into a 100 mL Schlenk flask equipped with a magnetic stirbar. n-Butanol (50 mL) was added to the flask under argon, and the suspension was heated to 80° C. for 18 hours. The solvent was removed under reduced pressure and the solid was recrystallized from dichloromethane and ether, and isolated on a frit. The product was washed with cold ether to yield 4.000 g of product (7.19 mmol, 91%). Single crystals for X-ray diffraction were grown from dichloromethane and ether in a glove box.

A reduced Fe catalyst ($^{p\text{-}methoxy}$PDI)(FeN$_2$) was prepared. Benzene and ether (25 mL of each) were added to a flask in a glove box. Hg (39.664 g, 0.198 mol) was added to the flask and the mixture was frozen in a cold well at −78° C. Sodium metal (0.207 g, 8.99 mol) was added to the mixture and the mixture was warmed to room temperature and stirred for 30 minutes. ($^{p\text{-}methoxy}$PDI)(FeCl$_2$) (1.000 g, 1.80 mmol) was added to the flask and the mixture was stirred at ambient temperature for 12 hours. After the reaction was complete, the mixture was filtered through CELITE® and the solvent was removed under a stream of nitrogen to give 0.751 g (79%) of the product.

Catalytic Reactions

For the catalytic reactions, scale-up reactions, and hydrogenation reactions, all air and moisture-sensitive steps were performed using Schlenk techniques on a dual manifold vacuum line under ultra-high purity argon or in an inert atmosphere glove box containing an atmosphere of purified nitrogen. Air and moisture free solvents were dried over 3 Å molecular sieves before use. Deuterated solvents for NMR spectroscopy were dried over 3 Å molecular sieves before use. [($^{Me}$PDI)Fe(N$_2$)]2(μ$_2$-N$_2$), [($^{iPr}$PDI)Fe(N$_2$)]2(μ$_2$-N$_2$), and 4-Methoxy-2,6-dimethylaniline were prepared by literature methods. Alkene substrates were purified by distillation over CaH$_2$ under an inert atmosphere.

$^1$H NMR and $^{13}$C NMR spectra were recorded using a Bruker 300 MHz ($^1$H), 75 MHz ($^{13}$C) spectrometer and referenced to the residual solvent peaks. The mixtures and pure compounds were analyzed via Gas Chromatography—Flame Ionization Detector (GC/FID) equipped with a RTX-5MS 30-meter column under the following conditions: inlet temperature, 250° C.; initial column temperature, 40° C.; 1st temperature ramp, 4° C./min to 100° C.; 2nd temperature ramp, 20° C./min to 300° C.

In all of the catalyst reactions below, 1 mol % of an Fe-based catalyst (e.g. ($^{Me}$PDI)Fe(N$_2$)]2(μ$_2$-N$_2$)) was added into a 3 mL vial equipped with a Teflon cap and stir bar in a glove box. Substrates were added neat to the vial and the reaction was monitored with GC/FID. In the case of mixed coupling reactions, equal molar quantities of each substrate were used (i.e. 50:50 when two substrates were used). After the reaction had stopped, the vial was removed from the glove box and the reaction mixture was diluted with pentane. The extract was filtered through silica and the solvent and starting material were removed under reduced pressure. Every reaction formed a mixture of an alkyl cyclobutane and an alkene dimer that was confirmed through $^1$H NMR and $^{13}$C NMR spectroscopy. Table 1 below shows the results of each reaction of an alpha olefin or mixture of alpha olefins with a catalyst to form a mixture of hydrocarbons. Table 1 lists the reaction, conversion % (con. %), $^1$H NMR (CDCl$_3$), $^{13}$C NMR (CDCl$_3$), analytical calculation (calc.), and found.

TABLE 1

Results of one or more alpha olefins reacting with a catalyst.

| Reaction | Con. % | $^1$H NMR (CDCl$_3$) | $^{13}$C NMR (CDCl$_3$) | Calc. | Found |
|---|---|---|---|---|---|
| Dimerization of 1-pentene | 87% | δ = 4.70 (bd, = CH$_2$, J = 8 Hz), 2.01-1.73 (m, CH$_2$), 1.51-1.14 (m, CH$_2$), 0.97-0.79 (m, CH$_3$) | δ = 42.3, 39.0, 34.1, 24.9, 22.3, 20.5, 14.3, 14.0 | C$_{10}$H$_{20}$: C, 85.63 H, 14.37 | C$_{10}$H$_{20}$: C, 85.34 H, 14.32 |
| Dimerization of 1-hexene | 82% | δ = 4.70 (bd, = CH$_2$), 2.01-1.71 (m, CH$_2$), 1.51-1.09 (m, CH$_2$), 0.95-0.80 (m, CH$_3$) | — | | |
| Mixed coupling of pentene and hexene (1:1) | 82% | δ = 4.70 (bd, = CH$_2$), 2.03-1.70 (m, CH$_2$), 1.51-1.08 (m, CH$_2$), 0.97-0.74 (m, CH$_3$) | — | C$_{10}$H$_{20}$, C$_{11}$H$_{22}$, C$_{12}$H$_{24}$: C, 85.63 H, 14.37 | C$_{10}$H$_{20}$, C$_{11}$H$_{22}$, C$_{12}$H$_{24}$: C, 85.83 H, 14.42 |
| Mixed coupling of pentene and isoprene (1:1) | 88% | δ = 5.27-5.12 (m, CH$_2$), 4.81-4.57 (m, CH$_2$), 2.79-2.54 (m, CH), 2.34-1.93 (m, CH), 1.85-1.60 (m), 1.54-1.40 (m, CH$_2$), 1.38-1.14 (m, CH$_3$), 1.01-0.81 (m, CH$_3$) | δ = 149.8, 149.4, 132.8, 122.3, 109.0, 107.4, 107.2, 39.6, 38.6, 38.5, 38.3, 35.0, 33.9, 33.2, 31.8, 31.2, 30.8, 25.9, 21.0, 20.5, 20.3, 17.7, 14.5, 14.3, 14.2, 14.0 | | |
| Mixed coupling of hexene and isoprene (1:1) | 85% | δ = 5.22-5.14 (m, CH$_2$), 4.75-4.69 (m, CH$_2$), 4.69-4.66 (m), 4.63-4.60 (m), 2.77-2.56 (m, CH), 2.28-2.14 (m, CH), 2.14-1.92 (m, CH$_2$), 1.75-1.73 (m), 1.70-1.69 (m), 1.67-1.65 (m), 1.63, (bs, CH$_3$), 1.52-1.11 (m, CH$_2$), 0.97-0.84 (m, CH$_3$) | — | | |

TABLE 1-continued

Results of one or more alpha olefins reacting with a catalyst.

| Reaction | Con. % | $^1$H NMR (CDCl$_3$) | $^{13}$C NMR (CDCl$_3$) | Calc. | Found |
|---|---|---|---|---|---|
| Mixed coupling of isoprene, hexene, and pentene (2:1:1) | 80% | δ = 5.21-5.13 (m, CH$_2$), 4.74-4.65 (m, CH$_2$), 4.60 (bs), 2.73-2.54 (m, CH), 2.27-2.14 (m, CH$_2$), 2.14-1.95 (m, CH), 1.72 (bs, CH$_3$), 1.68 (bs), 1.64 (bs), 1.62 (bs), 1.51-1.36 (m, CH$_2$), 1.36-1.11 (m, CH$_2$), 0.95-0.81 (m, CH$_3$) | — | | |

Scaled-Up Reactions

In the scaled-up reactions, a 2 mol % catalyst was combined with at least one alpha olefin in a 20 mL Teflon capped vial. The neat mixture was stirred and monitored using GC/FID until the reaction stopped. The mixture was then diluted with pentane, filtered through a silica plug, and the solvent was removed under reduced pressure. Each reaction formed an alkyl cyclobutane product that was confirmed through $^1$H NMR and $^{13}$C NMR spectroscopy. The results of each reaction are shown below in Table 2.

TABLE 2

Scaled-up reaction results.

| Alpha olefin(s) | Catalyst | Amount | Yield |
|---|---|---|---|
| Pentene/pentene | 0.341 g, 0.73 mmol | 1-pentene (5.120 g, 73 mmol) | 4.240 g (83%) |
| Hexene/hexene | 0.555 g, 1.2 mmol | 1-hexene (10.000 g, 118.8 mmol) | 9.341 g (93%) |
| Hexene/isoprene | 0.555 g, 1.2 mmol | 1-hexene (5.050 g, 60 mmol); isoprene (4.087 g, 60 mmol) | 8.290 g (90%) |

Hydrogenation of Mixtures

PtO$_2$ (200 mg) was added to the alkyl cyclobutane mixtures dissolved in THF (100 mL) in a glass bomb. The atmosphere was exchanged with hydrogen three times and the pressure was increased to 45 psi. The reaction flask was then shaken at ambient temperature for 18 hours. The mixture was filtered through CELITE® and the solvent was removed under reduced pressure. The final product was purified by vacuum distillation. The results of each reaction are shown in Table 3.

TABLE 3

Hydrogenation reactions.

| Product | Yield | Analytical Calculation | Found |
|---|---|---|---|
| Hydrogenated pentene dimers | 78% | C$_{10}$H$_{20}$, C$_{10}$H$_{22}$: C, 85.48; H, 14.52 | C$_{10}$H$_{20}$, C$_{11}$H$_{22}$: C, 85.34; H, 14.46 |
| Hydrogenated hexene dimers | 92% | C$_{12}$H$_{24}$, C$_{12}$, H$_{26}$: C, 85.51; H, 14.49 | C$_{12}$H$_{24}$, C$_{12}$, H$_{26}$: C, 85.34; H, 14.44 |
| Hydrogenated hexene/isoprene mixture | 94% | C$_{22}$, H$_{26}$: C, 85.07; H, 14.93 | C$_{22}$, H$_{26}$: C, 84.40; H, 14.24 |

Physical Properties of the Alkyl Cyclobutane Fuels

The density, viscosity, volumetric net heat of combustion (NHOC), gravimetric NHOC, and freezing point were all determined from testing or calculations for the three hydrogenated mixtures previously listed in Table 3. NHOC measurements were conducted by the Southwest Research Institute using ASTM D240N. The dynamic viscosity of the hydrogenated products was measured at −20° C. with a Brookfield DV-II+ Pro viscometer equipped with a small sample adaptor. Ethylene glycol was used as a standard in the laboratory to confirm the accuracy of the instrument. Samples were placed in the small sample adaptor and allowed to equilibrate at a given temperature for a minimum of 20 minutes prior to the viscosity being measured. The temperature was held to within ±0.05° C. with a constant temperature bath (Brookfield TC-502). The viscosity was then measured as outlined in ASTM D2983. Each measurement was performed in triplicate, and the reported data are an average of the triplicate readings.

Table 4 below shows the results for the density at 20° C. in g/mL, volumetric NHOC in kBtu/gal, gravimetric NHOC in MJ/kg, the viscosity at −20° C. in mm$^2$ s$^{-1}$, and the freezing point in ° C. for the three fuels. The dodecane and decane physical properties were calculated or obtained from the literature. Values for Jet-A, JP-5, and JP-8 are obtained from their respective specifications.

TABLE 4

Fuel properties.

| Fuel | Density (20° C., g/mL) | Volumetric NHOC (kBtu/gal) | Gravimetric NHOC (MJ/kg) | Viscosity (mm$^2$s$^{-1}$; −20° C.) | Freezing Point (° C.) |
|---|---|---|---|---|---|
| 1-pentene "PD" | 0.767 | 120.4 | 43.8 | 2.38 | <−80° C. |
| 1-hexene "HD" | 0.779 | 120.6 | 43.1 | 4.78 | <−80° C. |
| 1-hexene/ isoprene "HI" | 0.783 | 120.5 | 42.9 | 3.14 | <−80° C. |
| Dodecane | 0.750[a] | 118.6[b] | 44.1 | Solid | −10° C. |
| Decane | 0.730[c] | 116.4[d] | 44.4 | 2.55[e] | −30° C. |
| Jet A | ~0.81 | ~125 | >42.8 | <8.0 | −40° C. |
| JP-5 | 0.788-0.845 | ~125 | >42.8 | <8.5 | −46° C. |
| JP-8 | 0.775-0.840 | ~125 | >42.8 | <8.4 | −47° C. |

[a]Calculated from Caudwell, D. R.; Trusler, J. P. M.; Vesovic, V.; Wakeham, W. A. Int. J. Thermophys. 2004, 25, 1339-1352.
[b]Calculated from Gollis, M. H.; Belenyessy, L. I.; Gudzinowicz, B. J.; Koch, S. D.; Smith, J. O.; Wineman, R. J. J. Chem Eng. Data 1962, 7, 311-316.
[c]Calculated from Caudwell, D. R.; Trusler, J. P. M.; Vesovic, V.; Wakeham, W. A. J. Chem. Engin. Data 2009, 54, 359-366.
[d]Calculated from Prosen, E. J.; Rossini, F. D. J. Res. NBS 1945, 263-267.
[e]Obtained from Giller, E. B.; Drickamer, H. G. Ind. Eng. Chem. 1949, 41,2067-2069.

As shown in Table 4, examples of the fuels produced above have an increased density compared to the conventional acyclic paraffins (i.e., dodecane and decane), which is due to the presence of cyclobutanes in the example fuel. The volumetric NHOC of the example fuels was also higher compared to acyclic paraffins of similar molecular weight. The increased volumetric and gravimetric NHOC is due to a combination of the increased density of the cyclic hydrocarbons, the lack of aromatic compounds, and the ring strain of the cyclobutane groups in the example fuel.

In addition, examples of the fuels above have a decreased viscosity and lower freezing point compared to the acyclic paraffins with similar molecular weight. Due to chain branching in the example fuels prepared herein, the viscosities and freezing points of the fuels are lower than acyclic paraffins with similar molecular weight and conventional jet fuel.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Unless otherwise stated, any feature described herein can be combined with any aspect or any other feature described herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range. For example, a range from about 1 atm to about 400 atm should be interpreted to include not only the explicitly recited limits of from about 100 atm to about 200 atm, but also to include individual values, such as 125 atm, 150 atm, 175 atm, etc., and sub-ranges, such as from about 135 atm to about 175 atm, etc.

In describing and claiming the examples disclosed herein, the singular forms "a", and "the" include plural referents unless the context clearly dictates otherwise.

What is claimed is:

1. An alkyl cyclobutane fuel, comprising:
A chemical formula, wherein the chemical formula is:

where R and R' are each independently selected from the group consisting of cyclopropyl, cyclobutyl, cyclopen-
tyl, cyclohexyl, —CH$_2$-cyclopropyl, —CH$_2$-cyclobutyl, —CH$_2$-cyclopentyl, —CH$_2$-cyclohexyl, and combinations thereof.

2. The alkyl cyclobutane fuel of claim 1, wherein the alkyl cyclobutane fuel has a density equal to or greater than 0.767 g/mL.

3. The alkyl cyclobutane fuel of claim 1, wherein the alkyl cyclobutane fuel has a volumetric net heat of combustion equal to or greater than 120.0 kBtu/gal.

4. The alkyl cyclobutane fuel of claim 1, wherein the alkyl cyclobutane fuel has a gravimetric net heat of combustion equal to or greater than 42.8 MJ/kg.

5. The alkyl cyclobutane fuel of claim 1, wherein the alkyl cyclobutane fuel has a freezing point of at least −80° C.

6. The alkyl cyclobutane fuel of claim 1, wherein the alkyl cyclobutane fuel consists of 1,2-alkylcyclobutane, 1,3-alkylcyclobutane, or combinations thereof.

7. The alkyl cyclobutane fuel of claim 1, wherein R and R' are each independently selected from the group consisting of —Clb-cyclopropyl, —Clb-cyclobutyl, -Of-cyclopentyh —CH2-cyclohexyl, and combinations thereof.

8. An alkyl cyclobutane fuel, consisting of:
A chemical formula, wherein the chemical formula is:

where R and R' are each independently selected from the group consisting of cyclopropyl, cyclobutyl, cyclopentyl, cyclohexyl, —CH$_2$-cyclopropyl, —CH$_2$-cyclobutyl, —CH$_2$-cyclopentyl, —CH$_2$-cyclohexyl, and combinations thereof.

9. A method for making alkyl cyclobutane fuel, comprising:
Obtaining a solution of at least one alpha olefin;
Adding a catalyst to the solution, thereby generating a mixture of dimers;
hydrogenating the mixture, thereby converting the dimers to hydrogenated dimers; and
Purifying the mixture to produce the alkyl cyclobutane fuel of claim 1.

10. The method of claim 9, wherein the alpha olefin includes about 3 to about 20 carbon atoms.

11. The method of claim 10, wherein the alpha olefin is selected from the group consisting of ethylene, propylene, 1-butene, 1-pentene, 1-hexene, 1-heptene, 1-octene, 1-nonene, 1-decene, and combinations thereof.

12. The method of claim 10, wherein the alpha olefin has at least one hydrocarbon chain branch.

13. The method of claim 10, wherein the alpha olefin is selected from the group consisting of isoprene, vinylcyclobutane, allylcyclobutane, vinylcyclopropane, allylcyclopropane, vinylcyclopentane, allylcyclopentane, vinylcyclohexane, allylcyclohexane, 3-methylbut-1-ene, α-olefin branched chain isomers of 1-hexene, 1-heptene, 1-octene, 1-nonene, and 1-decene, and combinations thereof.

14. The method of claim 9, wherein the catalyst is an Fe-based or a Co-based catalyst coordinated to a diimine pyridine pincer ligand.

15. The method of claim 14, wherein the diimine pyridine pincer ligand is (1E,1'E)-1,1'-(pyridine-2,6-diyl)bis(N-(4-methoxy-2,6-dimethylphenyl)ethan-1-imine) ($^{p\text{-}methoxy}$PDI).

16. The method of claim 9, wherein the dimers are alkyl cyclobutanes or a combination of alkyl cyclobutanes and alkene dimers.

17. The method of claim 16, wherein the alkyl cyclobutanes are present in an amount ranging from about 50% to about 98% based on a total % of dimers in the mixture of dimers.

18. The method of claim 16, wherein the alkyl cyclobutanes are 1,2-alkylcyclobutane, 1,3-alkylcyclobutane, or combinations thereof.

19. The method of claim 9, wherein the catalyst is reacted with the alpha olefin in the solution at a pressure ranging from about 1 atm to about 400 atm, for a time ranging from about 1 hour to about 150 hours, and at a temperature ranging from about 0° C. to about 80° C.

20. The method of claim 16, wherein the alkene dimers form branched alkanes after hydrogenating the mixture.

21. The method of claim 9, wherein hydrogenating is performed in the presence of hydrogen gas and a catalyst based on a transition metal selected from the group consisting of Ni, Pd, Pt, Ru, Cu, Zn, and combinations thereof.

22. The method of claim 9, wherein hydrogenating is performed at a pressure ranging from about 1 atm to about 200 atm and a temperature ranging from about 25° C. to about 200° C.

23. The method of claim 9, wherein the alkyl cyclobutane fuel consists of a density of greater than 0.767 g/mL, a volumetric net heat of combustion of greater than 120.0 kBtu/gal, a gravimetric net heat of combustion of greater than 42.8 MJ/kg, a kinematic viscosity at −20° C. of less than 4.78 $mm^2 \, s^{-1}$, and a freezing point of less than −80° C.

24. A method for making an alkyl cyclobutane fuel, comprising:

Obtaining a solution of at least one alpha olefin;

Adding a catalyst to the solution, thereby generating a mixture of at least one alkyl cyclobutane; and Purifying the mixture to produce the alkyl cyclobutane fuel of claim 20.

25. The method of claim 24, wherein the alkyl cyclobutane is 1,2-alkylcyclobutane, 1,3-alkylcyclobutane, or combinations thereof.

* * * * *